United States Patent [19]

Mueller et al.

[11] Patent Number: 4,835,190

[45] Date of Patent: May 30, 1989

[54] PHENOLIC THIOETHERS AS INHIBITORS OF 5-LIPOXYGENASE

[75] Inventors: Richard A. Mueller, Glencoe; Richard A. Partis, Evanston, both of Ill.

[73] Assignee: G. D. Searle & Co., Chicago, Ill.

[21] Appl. No.: 58,429

[22] Filed: Jun. 5, 1987

[51] Int. Cl.[4] ............... A61K 31/05; A61K 31/10; A61K 31/095

[52] U.S. Cl. .................. 514/706; 514/708; 514/731

[58] Field of Search ............ 514/706, 708, 731

[56] References Cited

U.S. PATENT DOCUMENTS

| | | | |
|---|---|---|---|
| 3,886,285 | 5/1975 | Bentley et al. | 514/708 |
| 4,012,523 | 3/1977 | Wagner . | |
| 4,029,812 | 6/1977 | Wagner et al. . | |
| 4,076,841 | 2/1978 | Wagner et al. . | |
| 4,078,084 | 3/1978 | Wagner et al. . | |
| 4,128,530 | 12/1978 | Cottman et al. . | |
| 4,143,076 | 3/1979 | Cottman et al. . | |
| 4,153,803 | 5/1979 | Thiele et al. . | |

OTHER PUBLICATIONS

Chem. Abst. 89 (1978)-27167j.
Chem. Abst. 94 (1981)-30290c.
M. B. Neuworth, *J. Med. Chem*, 13 (4): 722-5.
Chem. Abst. 76:109226y; vol. 76 (1972).
Chem. Abst. 84:6258w; vol. 84 (1976).
Chem. Abst. 83: 27876r, vol. 83 (1975).
Samuelsson, "Leukotrienes: Mediators of Immediate Hypersensitivity Reactions and Inflammation", *Science*, v. 220, 1983, pp. 568-570.
Bach, "Inhibitors of Leukotrinee Synthesis and Action", *The Leukotrienes, Chemistry and Biology*, Academic Press, pp. 163-194 (1984).
Lee et al., "Human Biology and Immunoreactivity of Leukotrienes", *Advances in Inflammation Research*, vol. 6, pp. 219-225, Raven Press (1984).
Editorial, "Leukotrienes and Other Lipoxygenase Products in the Pathegonesis and Therapy of Psoriasis and Dermatoses", *Arch. Dermatol.*, vol. 119, pp. 541-547 (Jul. 1983).
Lewis et al., "A Review of Recent Contributions on Biologically Active Products of Arachidonate Conversion", *Int. J. Immunopharma.* vol. 4, No. 2, pp. 85-90 (1982).
Bach, "Prospects for the Inhibition of Leukotriene Synthesis", Biochemical Pharmacology, vol. 33, No. 4, pp. 515-521 (1984).
Becker, "Chemotactic Factors of Inflammation", pp. 223-225 (Elsevier Science Publishers, B.V. Amsterdam, 1983).
Sharon et al., "Enhanced Synthesis of Leukotriene $B_4$ by Colonic Mucosa in Inflammatory Bowel Disease", Gastroenterology, vol. 86, pp. 453-460 (1984).
Musch et al., "Stimulation of Colonic Secretion by Lipoxygenase Metabolites of Arachidonic Acid", *Science*, vol. 217, p. 1255 (1982).
Khim. Khim. Tekhnol. 20, (4), pp. 568-574 (1977).

*Primary Examiner*—Stanley J. Friedman
*Attorney, Agent, or Firm*—R. E. L. Henderson; Mary Jo Kanady; Paul D. Matukaitis

[57] ABSTRACT

The compounds of the present invention comprise substituted phenolic thioether derivatives that are specific inhibitors of 5-lipoxygenase and which, therefore, are useful in the treatment of local and systemic inflammation, allergy and hypersensitivity reactions and other disorders in which agents formed in the 5-lipoxygenase metabolic pathway are involved.

14 Claims, No Drawings

PHENOLIC THIOETHERS AS INHIBITORS OF 5-LIPOXYGENASE

BACKGROUND OF THE INVENTION

The present invention relates to substituted phenolic thioether derivatives and more particularly relate to the novel compounds of Formula I which are specific 5-lipoxygenase inhibitors and are useful, for example, as anti-inflammatory and anti-allergy agents.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects. The leukotrienes, which are produced via the 5-lipoxygenase pathway, are the major contributors to the onset of the symptoms of asthma, and mediators for immediate hypersensitivity reactions, inflammations and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by subtances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion and possibly that of tumor cells (metastasis). $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases. Examples of such proteases include elastase, cathepsin G., collagenase and the like.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathwhich which play a role in immediate hypersensitivity reactions and also have pronounced inflammatory effects. Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs. Co-administration of the 5-lipoxygenase inhibitors of this invention with protease inhibitors and/or cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides new chemical entities which are inhibitors of the 5-lipoxygenase pathway and are useful in the treatment of asthma, rheumatoid arthritis, psoriasis, inflammatory bowel disease, nephritis, vasculitis, adult respiratory distress syndrome (ARDS) and other allergic, hypersensitivity, and inflammatory conditions.

See Bengt Samuelsson, "Leukotrienes: Mediators of Immediate Hypersensitivity Reactions and Inflammation", *Science*, 220, 568–575 (1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York 1984); Editorial, "Leukotrienes and other Lipoxygenase Products in the Pathogenesis and Therapy of Psoriasis and Dermatoses", *Arch. Dermatol*, 119, 541–547 (1983); Robert A. Lewis et al., "A Review of Recent Contributions on Biologically active Products of Arachidonate Conversion", Int. *J. Immunopharmac.* 4, 85–90 (1982); Miachael K. Bach, *Biochemical Pharmacology*, 23, 515–521 (1984); and E. L. Becker, *Chemotactic Factors of Inflammation*, pp 223–225 (Elsevier Science Publishers V.B., Amsterdam, 1983); P. Sharon, and W. F. Stenson, *Gastroenterology*, 84, 454 (1984); and M. W. Musch, et al., *Science*, 217, 1255 (1982).

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors such as the non-steroidal anti-inflammatory agents.

Various thioether compounds have been described previously. For example, CA 94 (5): 30290c, CA 76

(19): 109226y and CA 73 (9): 45047u disclose 2,6-bis(1,1-dimethylethyl)-4-(methylthio)phenol and CA 84 (2): 6258w and CA 73 (9): 45047u disclose 2,6-bis(1,1-dimethylethyl)-4-[(1,1-dimethylethyl)thio]-phenol, and CA 83 (3): 27876r discloses 2,6-bis(1,1-dimethylethyl)-4-(octylthio)-phenol.

U.S. Pat. Nos. 4,029,812, 4,076,841 and 4,078,084 disclose the compounds of the formula

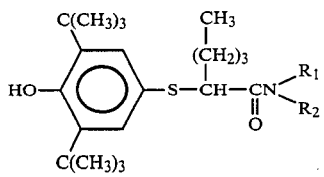

comprising 2-(3,5-ditert-butyl-4-hydroxyphenyl) thio carboxamides where $R_1$ and $R_2$ independently represent hydrogen, lower alkyl, lower alkoxy, hydroxy, or lower hydroxyalkyl. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tert-butyl-4-hydroxythiophenol, and hydrogen sulfide to acrylate derivatives have been described. See Medvedev et al., *Izv. Vyssh. Uchebn. Zaved., Khim. Khim. Tekhnol.*, 20, 568–574 (1977). The compounds resulting from the foregoing processes have the general formula $RS(CH_2)_nX$ and $S(CH_2CH_2X)_2$ in which R is 3,5-di-tert-butyl-4-hydroxphenyl and X represents, for example, —C≡N, $NH_2$, $CH(OH)CH_2Cl$, OH, COCl, and various carboxy, carboxylate and amide functions. Compounds of formula I according to the present invention or 5-lipoxygenase activity for structurally related compounds are not disclosed.

U.S. Pat. No. 4,153,803 discloses cholesterol-lowering phenoxyalkanoic acid esters of the formula

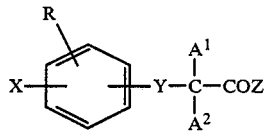

wherein, when Y is sulfur, X is hydrogen, benzyl, benzyloxy, benzylthio, or substituted derivatives thereof; R is hydrogen, halogen, hydroxy, alkyl, or alkoxy; $A^1$ and $A^2$ are hydrogen or alkyl; and Z is amine or azacyclohydrocarbyloxy, alkoxy, hydroxy, O—M+ where M is a cation, cycloalkoxy, tertiaryaminoalkoxy, pivaloyloxyalkoxy or pyridyl-C-alkoxy.

SUMMARY OF THE INVENTION

It is, therefore, a primary object of the present invention to provide novel substituted phenolic thioether derivatives.

It is a further object of the present invention to provide methods for promoting anti-allergic and anti-inflammatory effects in mammals in need thereof by the administration of preselected dosages of the compounds of the present invention or pharmaceutically acceptable salts thereof in appropriate non-toxic pharmaceutical dosage forms or compositions.

Another object of the present invention is to provide unit dosage forms adapted for, e.g., oral or parenteral administration. Such dosage forms would be useful in the treatment, management, and mitigation of allergies, inflammation, hypersensitivity reactions, and related disorders and conditions in which physiologically active agents formed in the 5-lipoxygenase metabolic pathway are involved.

DETAILED DESCRIPTION OF THE PREFERRED EMBODIMENTS

These and other similar objects, advantages and features are accomplished according to the products, compositions and methods of the invention comprised of compounds of the formula

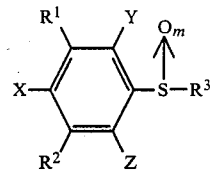

or a pharmaceutically acceptable base addition salt thereof; wherein $R^1$ and $R^2$ are independently $C_4$–$C_{10}$ tert-alkyl;

$R^3$ is $C_1$–$C_6$ alkyl;

X, Y, and Z are independently:
(a) hydrogen;
(b) hydroxy; or
(c) $C_1$–$C_4$ alkoxy, with the proviso that at least one of X, Y, and Z is hydroxy or $C_1$–$C_4$ alkoxy; and m is 0 or 1.

The term "$C_1$–$C_6$ alkyl" refers to straight or branched chain alkyl groups having from 1 to 6 carbon atoms, also referred to as lower alkyl. Examples of $C_1$–$C_6$ alkyl are methyl, ethyl, propyl, butyl, pentyl, hexyl, and the isomeric forms thereof.

The term "$C_1$–$C_4$ alkoxy" refers to straight or branched chain alkoxy groups having from 1 to 4 carbon atoms. Examples of $C_1$–$C_4$ alkoxy are methoxy, ethoxy, propoxy, butoxy, and the isomeric forms thereof.

The term "$C_4$–$C_{10}$ tert-alkyl" as used herein in reference to $R^1$ and $R^2$ refers to branched chain alkyl moieties of from 4 to 10 carbon atoms having a tertiary carbon atom attached to the phenyl ring substituted by $R^1$ and $R^2$. Examples of such groups are tert-butyl (i.e., 1,1-dimethylethyl), 1,1-dimethylpropyl, 1-methyl-1-(ethyl)pentyl, 1,1-diethylpropyl, 1-ethyl-1-(propyl)butyl, and the like.

The term "pharmaceutically acceptable base addition salt" refers to a salt prepared by contacting a compound of Formula I with a base whose cation is generally considered suitable for human consumption. Examples of pharmaceutically acceptable addition salts include lithium, sodium, potassium, magnesium, calcium, titanium, tetraalkylammonium and guanidinium salts.

It will be appreciated by those skilled in the art that when $R^3$ in Formula I represents branched chain alkyl or m is 1, one or more asymmetric centers may exist and accordingly enantiomers or diastereomers and mixtures may be obtained. The present invention includes such mixtures as well as the separate isomers.

The preferred embodiments of this invention include compounds of the following general structure:

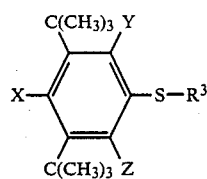

or a pharmaceutically acceptable base addition salt thereof; wherein $R^3$ is $C_1$-$C_6$ alkyl, X is hydroxy, and Y and Z are each hydrogen; or wherein $R^3$ is $C_1$-$C_6$ alkyl, X is hydrogen, and Y and Z are each hydroxy.

The most preferred embodiments of this invention include compounds of the following general structure:

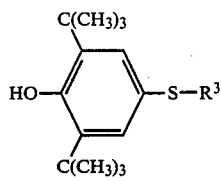

wherein $R^3$ is $C_1$-$C_6$ alkyl.

The compounds of the present invention can be administered in such oral dosge forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alignate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of this invention may be prepared by the methods illustrated in the following Schemes. Unless otherwise specified, the various substituents are defined as for Formula I, above. Scheme A illustrates a general method for preparing substituted phenolic thioethers of this invention.

SCHEME A

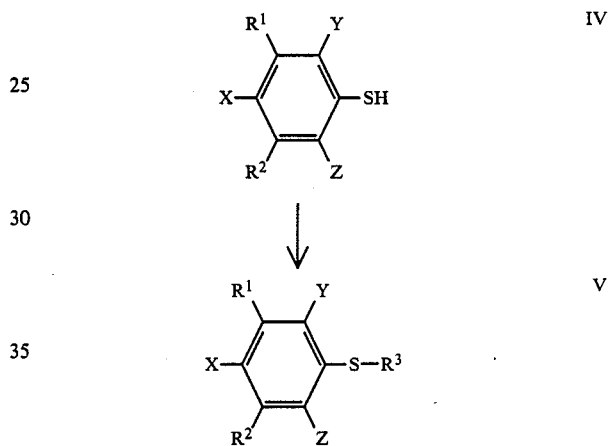

Alkylation of disubstituted 4-mercaptophenols of Formula IV with suitable alkylating reagents using methods known to those skilled in the art yields thioethers of Formula V. Preferred alkylation conditions involve stirring a compound of Formula IV with a suitable alkylating reagent in an suitable organic solvent containing a suitable base. In a typical reaction, a sufficient quantity of base is added to neutralize the aromatic thiol group and, if desired, the phenolic hydroxyl groups before the alkylating reagent is added. Suitable alkyating reagents include alkyl halides and alkyl tosylates, where the halogen is preferably bromine. Suitable organic solvents are organic liquids in which reactants may be dissolved or suspended but which are otherwise chemically insert. Examples of suitable organic solvents include lower alchols, such as methanol, ethanol, or propanol; ketones, such as acetone or methyl ethyl ketone; esters, such as ethyl acetate; ethers and cyclic ethers, such as tetrahydrofuran; N,N-disubstituted amides, such as dimethylformamide; and other solvents known in the art. Preferred organic solvents include alcohols, acetone, dichloromethane, and dimethylformamide. Suitable bases for the reaction are chemical compounds that are sufficiently basic to prevent the reaction medium from becoming acidic but which do not themselves form significant quantities of byproducts by reaction with other chemical reagents or with reaction products. Examples of suitable bases include alkali metal bicarbonates, such as lithium, sodium, or potassium bicarbonate; alkali metal carbonates, such as lithium, sodium, or potassium carbonate; alkali metal alkoxides, such as lithium, sodium, or potassium methoxide or ethoxide; alkaline earth carbonates, such as calcium carbonate or barium carbonate; and tertiary amines, such as triethylamine, tributylamine, N-methylmorpholine, and the like. Preferred bases include sodium ethoxide or triethylamine.

Scheme B illustrates an alternative method for preparing substituted phenolic thioethers of this invention.

SCHEME B

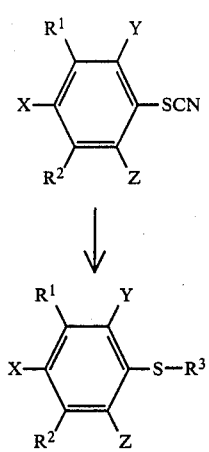

A mixture of thiocyanate of Formula VI, an alcohol of the formula $R^3OH$, and a trialkylphosphite can react to form a thioether of Formula V. Preferred reaction conditions involve heating the mixture, using an excess of the alcohol $R^3OH$ as solvent, at reflux. In some cases, it is advantageous to have the alkyl group in the trialkylphosphite be the same as $R^3$.

During the preparation of thiocyanates of Formula IV from phenols of Formula VII, certain substituted phenolic thioethers of Formula V may form as by-products. See Scheme C and Example 1. In general, an alcohol solvent of the formula $R^3OH$ gives rise to the group $R^3$ in compounds of Formula V.

SCHEME C

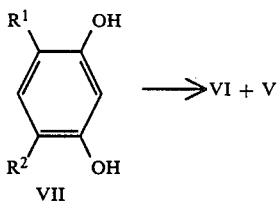

Scheme D illustrates a method for preparing sulfoxides, Formula VIII, of this invention and corresponding sulfones, Formula IX.

SCHEME D

V

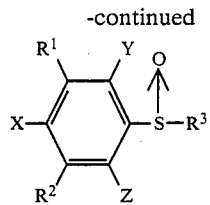

+/or

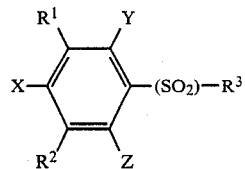

The sulfoxide compounds of this invention, Formula VIII, may be prepared by oxidation of the thioethers of Formula V using methods known to those skilled in the art. Commonly used oxidizing agents include, for example, peracids, such as m-chloroperoxybenzoic acid and percamphoric acid; peresters; peroxides, such as hydrogen peroxide; sodium metaperiodate; selenium dioxide; manganese dioxide; iodosobenzene; and the like. Optically active oxidants can provide optically active sulfoxides. Preferred conditions for preparing sulfoxides of Formula VIII include oxidizing thioethers V with an approximately equimolar quantity of m-chloroperoxybenzoic acid in a suitable organic solvent. Suitable organic solvents for the oxidation include alkanes and cycloalkanes; aromatic hydrocarbons; halocarbons, such as chloroform, dichloromethane, ethylene dichloride, and the like; and other solvents known in the art. A preferred organic solvent is dichloromethane. Oxidation may optionally be quenched by adding dimethylsulfide or potassium bisulfite. The sulfoxides of Formula VIII may then be isolated and purified by methods known in the art, including recrystallization and chromatography.

Further oxidation of the sulfoxide compounds of Formula VIII yields corresponding sulfones of Formula IX. The sulfones may form in situ during the initial oxidation reaction of thioethers of Formula V especially if two equivalents of oxidant or used or may be prepared by a separate oxidation of isolates sulfoxides of Formula VIII. The sulfones of Formula IX may then be isolated and purified by methods known in the art, including recrystallization and chromatography. Where the sulfones of Formula IX are prepared along with sulfoxides of Formula VIII during the initial oxidation reaction, the preferred method of isolation is chromatography.

The following non-limiting examples further illustrate details for the preparation of the compounds of the present invention. Those skilled in the art will readily understand and appreciate that known variations of the conditions and procedures in the following preparative methods can be utilized. All temperatures are degrees Celcius unless otherwise noted. Melting points were determined on a Thomas-Hoover melting point apparatus and are uncorrected.

EXAMPLE 1

3,5-bis(1,1-dimethylethyl)-4-hydroxyphenyl thiocyanate

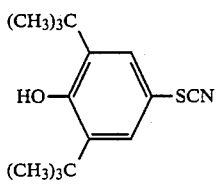

A mixture of 2,6-di-tert-butylphenol (474 g, 2.30 mole) and ammonium thiocyanate (76.12 g, 4.83 mole) in methanol (1200 ml) was stirred with cooling at 0° C. While the temperature was maintained at 0° to 10° C., chlorine gas was slowly bubbled through the mixture for about 1 hour, during which time the reaction mixture became a heterogeneous yellow color. Ammonia was then bubbled through the mixture for about 1.5 hours, during which time the reaction mixture was maintained at a temperature of between 0° to 10° C. The reaction was stirred for an additional hour at 0° C., poured into 2 liters of cold distilled water and refrigerated overnight. The aqueous phase was decanted, and the solid was taken up in methanol, precipitated by addition of water, filtered, and dried for 2 days over phosphorus pentoxide. The resulting gummy yellow solid was recrystallized from pentane and dried in vacuo to yield the product as a while powder, m.p. 61.5°–63° C. Analysis calc. for $C_{15}H_{21}NSO$:

Theory: C, 68.40; H, 8.03; N, 5.32; S, 12.17. Found: C, 68.85; H, 8.05; N, 5.29; S, 12.12.

EXAMPLE 2

2,6-bis(1,1-dimethylethyl)-4-mercaptophenol

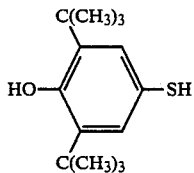

3,5-Bis(1,1-dimethylethyl)-4-hydroxyphenylthiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined and the solvents removed to yield a white powder. Recrystallization from methanol/water yielded, upon drying, 43.3 g of the title compound. The NMR spectrum confirmed the identity of the product.

EXAMPLE 3

2,6-bis(1,1-dimethylethyl)-4-(pentylthio)phenol

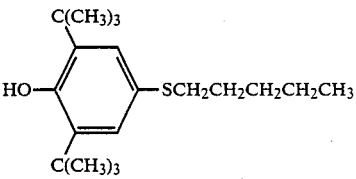

To a solution of freshly prepared sodium ethoxide (ca. 17 mmole) in ethanol (12 ml) was added with stirring 2,6-bis(1,1-dimethylethyl)-4-mercaptophenol (4.0 g, 17 mmol). After one hour, 1-chloropentane (4 ml, ca. 34 mmole) was added and the reaction mixture was stirred at room temperature for 20 hours. Water was added, and the mixture was extracted with diethyl ether. The ether layer was dried over magnesium sulfate, filtered, and concentrated in vacuo to an oil. Chromatography on silica gel and recrystallization from pentane gave the title compound, m.p. 54°–55°.

Analysis. Calcd. for $C_{19}H_{32}SO$: C, 73.95; H, 10.45; S, 10.39. Found: C, 74.19; H, 10.52; S, 10.64.

EXAMPLE 4

2,6-bis(1,1-dimethylethyl)-4-[(1-methylethyl)thio]-phenol

To a solution of 2,6-bis(1,1-dimethylethyl)-4-mercaptophenol (2.0 g, 8.4 mmole) in acetone (20 ml) was added sodium hydroxide (0.71 g, 17.6 mmole). After the sodium hydroxide had reacted, 2-bromopropane (1.08 g, 8.8 mmole) was added, and the reaction mixture was stirred for two hours. The mixture was concentrated in vacuo to an oil that was dissolved in diethyl ether (50 ml), washed with water (30 ml in two portions), dried over sodium sulfate, filtered, and concentrated in vacuo to a solid. Chromatography on silica gel and recrystallization from aqueous methanol gave the title compound, m.p. 80°–82°.

Analysis. Calcd. for $C_{17}H_{28}SO$: C, 72.80; H, 10.06. Found: C, 72.58; H, 9.87.

EXAMPLE 5

2,6-bis(1,1-dimethylethyl)-4-(methylthio)phenol

A mixture of 3,5-bis(1,1-dimethylethyl)-4-hydroxyphenylthiocyanate (238 g, 0.90 mole), triethylphosphite (225 g, 1.35 mole), water (200 g), and methanol (2000 ml) was stirred at reflux for two hours. Upon cooling, the mixture was concentrated in vacuo. The residue was triturated with water, and the solid was collected by filtration and air dried. Recrystallization from aqueous methanol gave the title compound, m.p. 69°–71°.

Analysis. Calcd. for $C_{15}H_{24}SO$: C, 71.38; H, 9.55; S, 12.70. Found: C, 71.28; H, 9.43; S, 12.79.

EXAMPLE 6

2,6-bis(1,1-dimethylethyl)-4-(methylsulfinyl)phenol

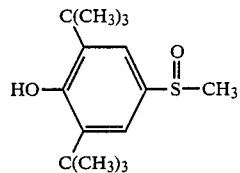

A mixture of 2,6-bis(1,1-dimethylethyl)-4-(methylthio)-phenol (1.0 g, 3.9 mmole) and meta-chloroperoxybenzoic acid (0.86 g, 4.1 mmole) in dichloromethane (25 ml) was stirred at room temperature for 20 hours. Water was added and the phases were separated. The organic layer was dried over magnesium sulfate, filtered, and concentrated in vacuo to dryness. Chromatography on silica gel gave the title compound, m.p. 171°–173°.

Analysis. Calcd. for $C_{15}H_{24}SO_2$: C, 67.12; H, 9.01; S, 11.94. Found: C, 67.01; H, 8.80; S, 11.73.

EXAMPLE 7

2,6-bis(1,1-dimethylethyl)-4-(methylsulfonyl)phenol

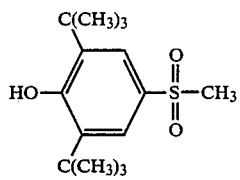

The title compound was prepared by the method of Example 6 using 2,6-bis(1,1-dimethylethyl)-4-(methylsulfinyl)phenol (1.0 g, 3.9 mmole) instead of 2,6-bis(1,1-dimethylethyl)-4-(methylthio)phenol. The organic layer was washed with water, dried over sodium sulfate, filtered and concentrated in vacuo. Chromatography on silica gel gave the title compound, m.p. 183°–187°.

Analysis. Calcd. for $C_{15}H_{24}SO_3$: C, 63.35; H, 8.51; S, 11.27. Found: C, 63.36; H, 8.40; S, 11.48.

EXAMPLE 8

2,6-bis(1,1-dimethylethyl)-1-methoxy-4-(methylthio)-benzene

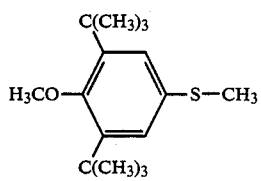

To a solution of 2,6-bis(1,1-dimethylethyl)-4-(methylthio)phenol (1.16 g, 4.6 mmole) in dimethylformamide (15 ml) was added sodium hydroxide (0.37 g, 9.2 mmole). After the solution was warmed for one hour, methyl iodide (0.72 g, 5.1 mmole) was added, and the mixture was warmed for an additional three hours. The reaction mixture was poured into water (150 ml) and extracted with diethyl ether (180 ml in three portions). The ether extract was washed with saturated aqueous sodium carbonate, dried over sodium sulfate, filtered, and concentrated in vacuo to an oil. Upon standing the oil crystallized. Recrystallization from hexane gave the title compound, m.p. 50°–52°.

Analysis. Calcd. for $C_{16}H_{26}SO$: C, 72.13; H, 9.34; S, 12.03. Found: C, 72.25; H, 9.20; S, 11.76.

EXAMPLE 9

4,6-bis(1,1-dimethylethyl)-2-(methylthio)-1,3-benzenediol

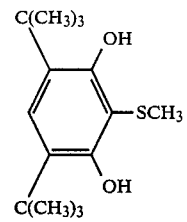

A mixture of 4,6-di-t-butylresorcinol (25.0 g, 112 mmole) and ammonium thiocyanate (18.0 g, 235 mmole) in methanol (100 ml) was stirred for 24 hours. The mixture was cooled to 0° and chlorine gas was bubbled through the solution for one hour. After the mixture was stirred for an additional hour at 0°, ammonia gas was bubbled through for one hour. A solid was removed by filtration and the filtrate was concentrated in vacuo. Chromatography on silica gel and recrystallization from hexane gave the title compound.

Analysis. Calcd. for $C_{15}H_{24}SO_2$: C, 67.12; H, 9.01; S, 11.94. Found: C, 67.00; H, 9.26; S, 11.94.

BIOLOGICAL EVALUATION

The compounds of the invention are evaluated with respect to 5-lipoxygenase inhibition according to the following assay procedure.

Inhibition of 5-lipoxygenase, in vitro: anti-inflammatory, anti-allergy activities. The 100,000 × g supernatant fraction of Rat Basophilic Leukemia Cell Homogenate (RBL-1) serves as a 5-lipoxygenase enzyme source. The enzyme is incubated with [1-$^{14}$C)-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value (inhibitor concentration to inhibit 50%).

The results with respect to certain of the preferred compounds of the present invention are set forth in Table I.

TABLE I

| Compound Example No. | 5-Lipoxygenase Inhibition, in vitro, IC$_{50}$ (μM) |
|---|---|
| 3 | 1.20 |
| 4 | 1.30 |
| 5 | 0.58 |
| 6 | 100.00 |

TABLE I-continued

| Compound Example No. | 5-Lipoxygenase Inhibition, in vitro, IC$_{50}$ ($\mu$M) |
| --- | --- |
| 7 | Inactive |
| 8 | 100.00 |
| 9 | 11.00 |

It is further noted that the compounds of the present invention have not been found to be effective inhibitors of either 12- or 15-lipoxygenases or of cyclooxygenase at concentrations which inhibit 5-lipoxygenase further confirming the specificity of the present compounds for 5-lipoxygenase.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A method for treating lipoxygenase mediated conditions in mammals comprising administering to a mammal in need of such treatment a therapeutically effective amount of a compound of the formula:

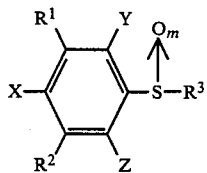

or a pharmaceutically acceptable base addition salt thereof; wherein $R^1$ and $R^2$ are independently $C_4$-$C_{10}$ tert-alkyl;

$R^3$ is $C_1$-$C_6$ alkyl;

X, Y, and Z are independently:
   (a) hydrogen;
   (b) hydroxy; or
   (c) $C_1$-$C_4$ alkoxy, with the proviso that at least one of X, Y, and Z is hydroxy or $C_1$-$C_4$ alkoxy; and m is 0 or 1.

2. A method according to claim 1 wherein said compound has the formula:

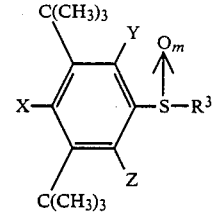

or a pharmaceutically acceptable base addition salt thereof; wherein $R^3$ is $C_1$-$C_6$ alkyl;

X, Y, and Z are independently:
   (a) hydrogen;
   (b) hydroxy; or
   (c) $C_1$-$C_4$ alkoxy, with the proviso that at least one X, Y, and Z is hydroxy or $C_1$-$C_4$ alkoxy; and m is 0 or 1.

3. A method according to claim 2 wherein said Compound has the formula:

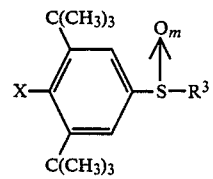

or a pharmaceutically acceptable base addition salt thereof; wherein $R^3$ is $C_1$-$C_6$ alkyl;

X is:
   (a) hydroxy; or
   (b) $C_1$-$C_4$ alkoxy; and m is 0 or 1.

4. A method according to claim 3 wherein X is hydroxy.

5. A method according to claim 4 wherein said compound has the formula:

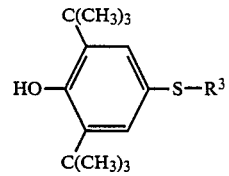

or a pharmaceutically acceptable base addition salt thereof; wherein $R^3$ is $C_1$-$C_6$ alkyl.

6. A method according to claim 5 wherein said compound is selected from the group consisting of:
2,6-bis(1,1-dimethylethyl)-4-(pentylthio)phenol,
2,6-bis(1,1-dimethylethyl)-4-[(1-methylethyl)thio]phenol, and
2,6-bis(1,1-dimethylethyl)-4-(methylthio)phenol.

7. A method according to claim 4 wherein said compound has the formula:

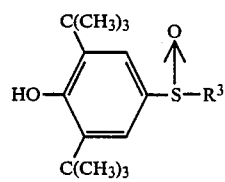

or a pharmaceutically acceptable base addition salt thereof; wherein $R^3$ is $C_1$–$C_6$ alkyl.

8. A method according to claim 7 wherein said compound is 2,6-bis(1,1-dimethylethyl)-4-(methylsulfinyl)-phenol.

9. A method according to claim 3 wherein X is $C_1$–$C_4$ alkoxy.

10. A method according to claim 9 wherein said compound has the formula:

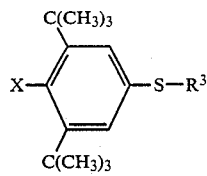

or a pharmaceutically acceptable base addition salt thereof; wherein $R^3$ is $C_1$–$C_6$ alkyl and X is $C_1$–$C_4$ alkoxy.

11. A method according to claim 10 wherein said compound is 2,6-bis(1,1-dimethylethyl)-1-methoxy-4-(methylthio)benzene.

12. A method according to claim 2 wherein said compound has the formula:

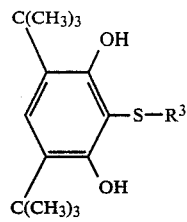

or a pharmaceutically acceptable base addition salt thereof; wherein $R^3$ is $C_1$–$C_6$ alkyl and m is 0 or 1.

13. A method according to claim 12 wherein said compound has the formula:

or a pharmaceutically acceptable base addition salt thereof; wherein $R^3$ is $C_1$–$C_6$ alkyl.

14. A method according to claim 13 wherein said compound is 4,6-bis(1,1-dimethylethyl)-2-(methylthio)-1,3-benzenediol.

* * * * *

UNITED STATES PATENT AND TRADEMARK OFFICE
CERTIFICATE OF CORRECTION

PATENT NO. : 4,835,190

DATED : May, 30 1989

INVENTOR(S) : Mueller, et al.

It is certified that error appears in the above-identified patent and that said Letters Patent is hereby corrected as shown below:

Column 1, lines 35-36, reading "imparied" should read -- impaired --.
Column 2, line 6, reading "pathwhich" should read -- pathway --.
Column 2, line 51, reading "Miachael" should read -- Michael --.
Column 3, line 18, reading "5-ditert-" should read -- 5-di-tert- --.
Column 3, line 32, reading "processes have the general formula" should read -- process have the general formula --.
Column 3, lines 33-34, reading "-hydroxphenyl" should read -- hydroxyphenyl --.
Column 5, line 26, reading "dosge" should read -- dosage --.
Column 6, line 7, reading "alignate" should read -- alginate --.
Column 6, line 55, reading "insert" should read -- inert --.
Column 6, line 56, reading "alchols" should read -- alcohols --.
Column 7, line 33, reading "of thiocyanate" should read -- of a thiocyanate --.
Column 7, lines 41-42, reading "Formula IV" should read -- Formula VI --.
Column 8, line 49, reading "or used" should read -- are used --.
Column 8, line 50, reading "isolates" should read -- isolated --.
Column 9, line 35, reading "while powder" should read -- white powder --.
Column 10, line 16, reading "mmol" should read -- mmole --.
Column 12, line 56, reading "inhibitor" should read -- inhibitory --.
Column 14, lines 17-18, reading "one X, Y, and Z" should read -- one of X, Y, and Z --.

Signed and Sealed this

Tenth Day of March, 1992

Attest:

HARRY F. MANBECK, JR.

*Attesting Officer*     *Commissioner of Patents and Trademarks*